United States Patent
Cheney, III et al.

[11] Patent Number: 5,534,020
[45] Date of Patent: Jul. 9, 1996

[54] INSTANT REUSABLE COMPRESS

[76] Inventors: Henry H. Cheney, III, 19 Charles St., Braintree, Mass. 02184; Michael Vecchione, 106 Banwell La., Mt. Laurel, N.J. 08054

[21] Appl. No.: 495,829

[22] Filed: Jun. 28, 1995

Related U.S. Application Data

[63] Continuation-in-part of Ser. No. 185,378, Jan. 24, 1994, abandoned.

[51] Int. Cl.⁶ ........................................ A61F 7/00
[52] U.S. Cl. ................ 607/108; 607/114; 62/4; 126/204; 383/901
[58] Field of Search ............... 607/96, 108–112; 126/204; 383/901; 62/4, 530; 165/46

[56] References Cited

U.S. PATENT DOCUMENTS

| | | | |
|---|---|---|---|
| 3,643,665 | 2/1972 | Caillouette | 607/114 |
| 3,804,077 | 4/1974 | Williams | 607/114 |
| 3,874,504 | 4/1975 | Verakas | 126/263 |
| 4,049,408 | 9/1977 | Patel | 206/219 |
| 4,081,256 | 3/1978 | Donnelly | 62/4 |
| 4,462,224 | 7/1984 | Dunshee et al. | 206/219 |
| 4,671,267 | 6/1987 | Stout | 607/114 |
| 4,964,402 | 10/1990 | Grim et al. | 607/111 |
| 4,967,573 | 11/1990 | Wilhelm | 62/530 |
| 5,447,531 | 9/1995 | Wood | 607/114 |

*Primary Examiner*—Angela D. Sykes
*Assistant Examiner*—Robert L. Nasser, Jr.
*Attorney, Agent, or Firm*—John P. McGonagle

[57] ABSTRACT

An instant reusable gel compress for applying cold or heat to a human or animal body part. The compress contains crystals of ammonium nitrate or calcium chloride, a water soluble acrylic polymer and an enclosed bag of water within a sealed, durable, flexible, plastic, bag-like container. When the interior water bag is broken, an immediate thermal reaction and simultaneous gel formation results. The resulting gel compress is then applied to the body part for cold or heat treatment. When the cold or heat is dissipated the gel compress itself may be chilled or heated again by an external source and then reused.

12 Claims, 2 Drawing Sheets

INSTANT REUSABLE COMPRESS

CROSS-REFERENCE

This is a continuation-in-part of Ser. No. 08/185,378, filed Jan. 24, 1994 now abandoned.

BACKGROUND OF THE INVENTION

This invention relates to instant reusable cold and hot compresses, and more particularly to reusable compresses capable of initially producing cold or heat by thermochemical reaction.

Instant compresses have long been used to apply cold or heat to human or animal body parts. Previous known compresses contain materials such as inorganic salts which chill or heat a fluid within the compress. The fluid used has generally been water or water mixed with chemicals possessing a high thermal capacity such as propylene glycol. The primary drawback of this technology is that these prior art instant compresses are not reusable. Also, the compresses eventually leak causing a loss of the internal fluid. Compresses which use high heat capacity chemicals such as propylene glycol have the added problem that the leaking fluid is toxic.

There are orthopedic devices in the prior art which are used to treat injured body parts by immobilizing the body part and applying cold or heat compresses. For example U.S. Pat. No. 4,964,402 discloses an orthopedic device for treatment of injured joints or limbs having at least one gel pad containing at least one phase change material for improving thermal energy storage capacity. The phase change material is pre-distributed throughout the gel matrix. Externally generated cold or heat is applied to the gel pad. The phase change material is selected so that it will undergo a phase change while the cold gel is reheating or the hot gel is cooling. In this manner, the U.S. Pat. No. 4,964,402 invention uses the latent heat of fusion of the phase change material to improve the heat capacity of the gel material. While the gel pad may be reused in the orthopedic device there is no means to provide an instant cooling or heating effect due to the method of dispersal of the phase change material. The orthopedic devices themselves are specialized to fit and immobilize specific body parts.

Inorganic salt hydrates combined with synthetic polymers to form a thermochemical energy storage material have been previously described. U.S. Pat. No. 4,574,051 describes the use of a hydrated salt suspended in synthetic polymers like polyvinyl alcohol, polyacrylic acid, polyethylene oxide and acrylamide polymers. In the U.S. Pat. No. 4,574,051 thermal storage device, only the latent heat of fusion of the salt hydrate is utilized. The patented device involved a material with an improved heat capacity. The inorganic salt would be pre-suspended in the synthetic polymer matrix hence ruling out any ability to create instant cold or heat effects.

The same is true for the thermal storage materials described in U.S. Pat. Nos. 4,273,667 and 4,545,916. In the U.S. Pat. No. 4,273,667, the thermal storage material is comprised of at least one hydrated compound, such as an inorganic salt, having a reversible transition to the anhydrous or less hydrated form and a hydrogel. The hydrogel was comprised of a water swollen cross linked polymer throughout which the hydrated compound was dispersed. Some of the polymers described in the U.S. Pat. No. 4,273,667 include a copolymer of acrylic acid with acrylamide. Calcium chloride was mentioned as a possible hydrated compound. Only the use of the salt heat of fusion was described in the U.S. Pat. No. 4,273,667 as the hydrated compound is pre-dispersed in the polymer matrix. U.S. Pat. No. 4,545,916 described a heat storage material in which sodium pyrophosphate decahydrate is dispersed throughout an open cell polymeric matrix. One of the polymeric matrices mentioned is formed by crosslinking a water soluble polymer having pendant carboxylic acid groups by means of cations of polyvalent metal or by a covalent crosslinking mechanism. The purpose of the phosphate salt is to improve the heat capacity of the polymer through the use of the salts heat of fusion. As the salt is pre-dispersed in the polymer matrix, the heat of the solution is not utilized.

There are many manufacturers of instant cold and hot compresses in North America and Europe. Their compresses are made with various types of flexible plastic containers which require them to be sealed on two or more sides. The process of sealing plastic is not an exact science resulting in containers which have a propensity to leak during or after activation. In the case of cold compresses this causes the patient to be put at risk of being subject to a frost bite burn from the escaping liquid which is at a temperature possibly as low as 15 degrees Fahrenheit. In the case of hot compresses, the patient may be exposed to a toxic liquid substance and the activated liquid which may have a temperature as high as 185 degrees Fahrenheit.

Prior art instant cold and hot compresses are made to be discarded after one use. If a patient tries to reuse a prior art compress by boiling the compress, placing it in a microwave oven, or placing it in a freezer, the compress bag-like container will usually break down because it is not made of a durable plastic material which will stand up to repeated use. Also, in the case of cold compresses, the compress when placed in a freezer will become hard and not have the ability to conform to the patient's body. Furthermore, should the compress leak the corrosive nature of the product may oxidize the metal finish of the inside of the freezer compartment.

Where attempts have been made to combine instant thermal reactions with a reusability feature, they have been limited. For example, U.S. Pat. No. 4,462,224 to Dunshee et al. discloses a three compartment, instant hot or cold, reusable cold pack for transferring heat to or from an object. A first compartment contains a solvent comprised primarily of water. A second compartment contains a particulate solute which is capable of dissolving in the first compartment solvent whereby a predetermined amount of heat is liberated or absorbed. The third compartment contains a gelling agent capable of gelling with the solvent and solute solution at ambient temperature. Mixing the contents of the first compartment and the second compartment provides an instant heating or cooling effect as in an instant hot or cold pack. Once the solution has returned to ambient temperature, the contents of the third compartment can be mixed with the contents of the first and second compartments to produce a gel. U.S. Pat. No. 4,967,573 to Wilhelm simplifies the Dunshee et al. pack with a two compartment construction. However, the gelling agent used is deliberately selected so that the agent will not actually form a gel until the cooling takes place and after the cold produced in the instant pack mode leaves the pack through normal use.

SUMMARY OF THE INVENTION

The primary objective of the present invention is to provide a compress with an initial instant thermal reaction combined with simultaneous gel formation, and residually a follow on reusable gel pack. This objective is accomplished by providing an interior water holding envelope within a larger envelope containing a dry, water soluble acrylic polymer powder mixed with an inorganic salt having either a negative or a positive heat of solution. The compress is activated by breaking the interior envelope thereby releasing water into the acrylic polymer/inorganic salt mix. Two, nearly simultaneous reactions take place. The inorganic salt and water mixture causes a thermal reaction, either heating or cooling. The acrylic polymer and water mixture forms a gel. These reactions occur simultaneously with full gel formation being accomplished in less than 90 seconds. After a period of time in use, approximately 1 hour, the thermal action reaches ambient temperature and the compress becomes a reusable gel pack.

The present invention uses the thermal effects of certain inorganic salts dissolving in water to provide an instant cooling or heating effect. A water soluble acrylic polymer almost instantly absorbs that water containing the inorganic salts to form a gel having a high relative thermal capacity. The acrylic polymer gel is enclosed in a durable, flexible, plastic, bag-like container which is then applied to a human or animal body part for instant therapy. Once the instant cold or heat dissipates the gel compress may be reused. The acrylic polymer gel has a viscosity such that it will not leak from the durable plastic container even if the container is punctured. The thermal fusion of the salt now dispersed in the acrylic polymer matrix enhances the materials thermal capacity. The gel compress and contents may be re-cooled or re-heated by external means and then reapplied to body parts. The gel substance viscosity is sufficient to permit the compress to conform to any body part.

The major advantage of the present invention is that if the flexible compress container is punctured or if a seal defaults, the liquid will not leak out. This has been the major complaint from users of prior art instant and reusable compresses. Compress containers containing the resulting gel of the instant invention have been punctured with sharp objects and the gel does not leak out of the container unless substantial pressure is applied to the container to force the gel from the container. The present invention resulting gel after activation has a PH factor of 6.5–7.0 which places it in the neutral range as compared to prior art devices which have an approximate acidic PH of 3.8. After the present invention compress is used, it may be reused by placing it in a freezer where the temperature is above 0 degrees Fahrenheit. A present invention hot compress may be reused by placing it in hot water or a microwave oven.

The present invention compress has the price economy of prior art instant compresses while providing the features of more expensive traditional reusable compresses. Furthermore, compresses made according to the present invention initially do not need an external thermal source for the compress to become cold or hot.

These together with other objects of the invention, along with various features of novelty which characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

DETAILED DESCRIPTION OF THE INVENTION

Figure 2:
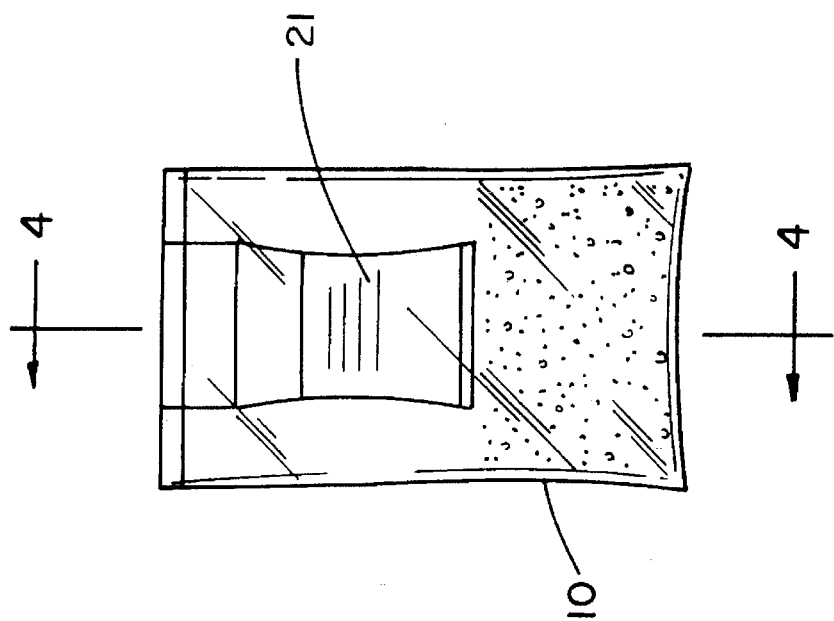
FIG. 2 is a front surface view of the compress shown in FIG. 1.
Figure 1:
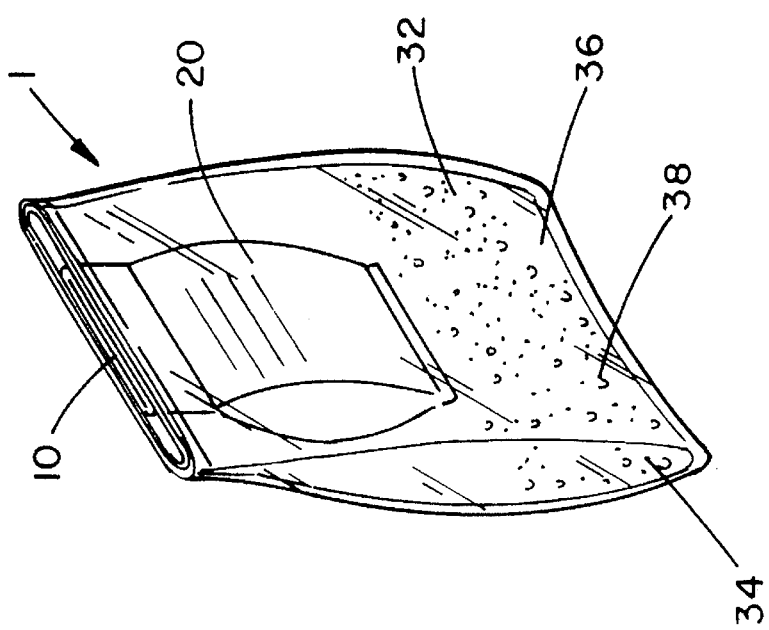
FIG. 1 is a perspective view of a compress according to the principles of the present invention.
Figure 5:
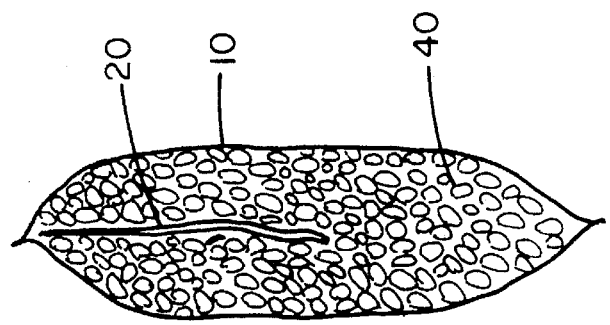
FIG. 5 is a view of the compress shown in FIG. 4 after activation.
Figure 4:
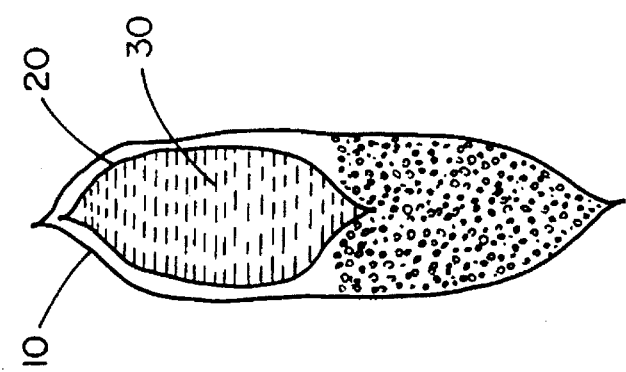
FIG. 4 is a vertical sectional view taken along the line 4—4 of FIG. 2.
Figure 3:
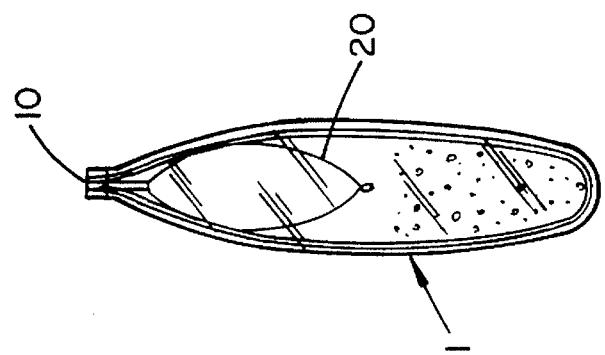
FIG. 3 is a side edge view of the compress shown in FIG. 1.

Referring to the drawings in detail wherein like elements are indicated by like numerals, there is shown an embodiment of the invention 1 composed of an outer, durable, flexible, bag-like, plastic container 10 containing within an interior saran-coated, polymylar plastic envelope 20 which in turn contains 4.5 ounces of colored tap water 30. The inner envelope 20 is scored on its exterior surface 2 so that it will break when a pressure of 25 pounds per square inch is applied to it. The outer durable plastic container 0 also contains within 3.5 ounces of ammonium nitrate 32 for a cold compress or 2.0 ounces of calcium chloride 34 for a hot compress. In addition, the outer container 10 contains within 0.5 to 4.0 ounces of crosslinked modified acrylic polymer (CMAP) 36 and 0.1 to 0.3 ounces of trisaminothane 38. When the inner envelope 20 filled with water 30 is ruptured, the water 30 mixes with the ammonium nitrate 32 or the calcium chloride 34 producing a thermal reaction resulting in either cold or heat being generated. The CMAP 36 and trisaminothane 38 simultaneously absorb the resulting liquid and form a gel mixture.

The instant reusable cold and hot gel compresses have two main parts, a larger durable plastic outer container 10 for gel containment and an inner envelope 20 containing water for activation of the inorganic salt and hydration of the water soluble acrylic polymer to form the gel matrix. The inner envelope 20 is relatively small, made out of a material durable enough not to break prematurely but weak enough to break releasing the water to the durable, flexible plastic outer container when direct pressure is applied. The outer durable plastic container 10 contains the inner water envelope 20, a water soluble acrylic polymer 36, an inorganic salt 32 or 34, and trisaminothane 38 as a thickening agent.

The inorganic salt in the instant reusable cold compress will be one with a negative heat of solution. When inorganic salts with negative heats of solution dissolve after the inner envelope is ruptured, there is an absorption of heat from the water, cooling the water. An endothermic reaction results when the inorganic salt dissolves.

The inorganic salt in the instant reusable hot compress will be one with a positive heat solution. When inorganic salts with positive heats of solution dissolve after the inner envelope of water is ruptured, there is a release of heat to the water, warming the water. An exothermic reaction results when the inorganic salt dissolves.

One of the known properties of some acrylic polymers is the ability of the polymers to absorb water. When the instantly cooled or heated water is mixed with such a water soluble acrylic polymer in the durable plastic container, a gel is formed. The inorganic salts will become dispersed throughout the gel matrix as the water is absorbed.

In the preferred embodiment of the instant reusable cold compress, the interior envelope contains 1 to 8 ounces of water with food coloring. Besides the inner envelope, the outer durable plastic container contains 0.15 to 1.2 ounces of a crosslinked modified acrylic polymer (CMAP) in grains of 50 to 4000 microns in diameter, an example of which is commercially sold by JRM Chemicals Inc. as SOIL MOIST HYDRO (tm), 1 to 8 ounces of ammonium nitrate as the inorganic salt with a negative heat of solution, and 1 to 2 cc of trisaminothane as a thickening agent. Although preferred, the trisaminothane is not required for the invention to function.

In the preferred embodiment of the instant reusable hot compress, the inner envelope contains 1 to 6 ounces of water with food coloring. Besides the inner envelope, the outer durable plastic envelope contains 0.3 to 0.6 ounces of a crosslinked modified acrylic polymer (CMAP) in grains of 50 to 4000 microns in diameter, an example of which is commercially sold by JRM Chemicals Inc. as SOIL MOIST (tm), 2 to 4 ounces of calcium chloride as the inorganic salt with a positive heat of solution, 0.5 to 1 cc of trisaminothane as a thickening agent. The calcium chloride has a positive heat of solution in all forms except the hexahydrate form. Although preferred, the trisaminothane is not required for the invention to function.

In use, direct pressure is applied to the interior water envelope causing it to break and release water into the outer durable plastic container. The inorganic salt will dissolve in the water causing the water to cool or heat depending on whether the gel compress is an instant cold or an instant hot gel compress. The water will hydrate the water soluble acrylic polymer (CMAP) forming the gel, and simultaneously cooling or warming the gel. The gel compress will then be applied to a human or animal body part. Due to the flexibility of the gel, the compress will be easy to wrap on the body part.

When initial use is complete the durable, flexible plastic outer container containing the gel matrix can be stored for reuse. The gel will prevent leakage of the solution in the event the outer container develops a perforation. When cooling reuse is desired, the gel compress can be externally chilled such as by refrigeration. The gel does not freeze hard but retains a gel-like viscosity, much like shaved ice. The gel compress can be reused for warming by externally heating it such as with microwave oven or placing it in hot water. The gel compress is then reapplied to a human or animal body part.

It is understood that the above embodiments using CMAP as the water soluble acrylic polymer, ammonium nitrate as the inorganic salt in the instant cold gel compress and calcium chloride as the inorganic salt in the instant hot gel compress are merely illustrative of the invention. Other embodiments may be readily devised by those skilled in the art which will embody the principles of the invention and fall with the spirit and scope thereof. For example, potassium iodate and/or urea may be substituted for the ammonium nitrate in the cold compress. Magnesium sulfate (anhydrous) may be substituted for calcium chloride in the hot compress. Sodium hydroxide and/or corn starch may be substituted for trisaminothane. Salts such as propylene glycol, ammonium chloride, potassium chloride and/or sodium chloride may be added to change the temperature of the initial thermal reaction.

We claim:

1. An instant reusable cold gel compress used for cooling a human or animal body part comprising:

a durable flexible outer container;

an interior breakable envelope contained within said flexible outer container;

water contained within said interior envelope;

a water soluble acrylic polymer contained within said flexible outer container;

an inorganic salt with a negative heat of solution contained within said flexible outer container;

wherein when said interior envelope is broken thereby releasing water into said flexible outer container, said water will dissolve said inorganic salt and hydrate said water soluble acrylic polymer, thereby forming a gel while cooling said gel.

2. An instant reusable cold gel compress as recited in claim 1, wherein:

said water soluble acrylic polymer is a crosslinked modified acrylic polymer.

3. An instant reusable cold gel compress as recited in claim 2, wherein:

said inorganic salt is ammonium nitrate.

4. An instant reusable cold gel compress as recited in claim 3, further comprising:

a thickening agent contained within said flexible outer container.

5. An instant reusable cold gel compress as recited in claim 4, wherein:

said thickening agent is trisaminothane.

6. An instant reusable cold gel compress as recited in claim 5, wherein:

said flexible outer container contains 0.15 to 1.2 ounces of said crosslinked modified acrylic polymer in grains of 50 to 4000 microns in diameter, 1 to 8 ounces of ammonium nitrate, and 1 to 2 cc of trisaminothane; and said interior breakable envelope contains 1 to 8 ounces of water.

7. An instant reusable hot gel compress used for applying warmth to a human or animal body part comprising:

a durable flexible outer container;

an interior breakable envelope contained within said flexible outer container;

water contained within said interior envelope;

a water soluble acrylic polymer contained within said flexible outer container;

an inorganic salt with a positive heat of solution contained within said flexible outer container;

wherein when said interior envelope is broken thereby releasing water into said flexible outer container, said water will dissolve said inorganic salt and hydrate said water soluble acrylic polymer, thereby forming a gel while warming said gel.

8. An instant reusable hot gel compress as recited in claim 7, wherein:

said water soluble acrylic polymer is a crosslinked modified acrylic polymer.

9. An instant reusable hot gel compress as recited in claim 8, wherein:

said inorganic salt is calcium chloride.

10. An instant reusable hot gel compress as recited in claim 9, further comprising:

a thickening agent contained within said flexible outer container.

11. An instant reusable hot gel compress as recited in claim 10, wherein:

said thickening agent is trisaminothane.

12. An instant reusable hot gel compress as recited in claim 11, wherein:

said flexible outer container contains 0.3 to 0.6 ounces of said crosslinked modified acrylic polymer in grains of 50 to 4000 microns in diameter, 2 to 4 ounces of calcium chloride, and 0.5 to 1 cc of trisaminothane; and said interior breakable envelope contains 1 to 6 ounces of water.

* * * * *